United States Patent [19]
Steltenkamp

[11] 4,093,565
[45] * June 6, 1978

[54] FLAVOR AND FRAGRANT COMPOSITIONS
[75] Inventor: Robert John Steltenkamp, Somerset, N.J.
[73] Assignee: Colgate-Palmolive Company, New York, N.Y.
[*] Notice: The portion of the term of this patent subsequent to Dec. 2, 1993, has been disclaimed.
[21] Appl. No.: 668,025
[22] Filed: Mar. 18, 1976

Related U.S. Application Data
[62] Division of Ser. No. 414,394, Nov. 9, 1973, Pat. No. 3,989,765, which is a division of Ser. No. 125,792, Mar. 18, 1971, abandoned.

[51] Int. Cl.$^2$ .................... A61K 7/46; C07C 1/20
[52] U.S. Cl. .................... 252/522; 260/601 R; 260/535 P; 426/533; 426/538; 260/666 A
[58] Field of Search ........... 260/601 R, 666 A, 535 P, 260/681, 675.5; 426/533, 538; 252/522

[56] References Cited
U.S. PATENT DOCUMENTS

| 556,944 | 3/1896 | Tiemann | 260/601 R |
| 3,294,550 | 12/1966 | Ikida | 260/601 R |

Primary Examiner—James O. Thomas, Jr.
Assistant Examiner—Werren B. Lone
Attorney, Agent, or Firm—Richard N. Miller; Murray M. Grill; Herbert S. Sylvester

[57] ABSTRACT

A method of making a synthetic lime mix having the fragrance of steam distilled lime oil comprising the steps of refluxing a mixture of citral or a citral containing oil and water in the presence of an acid catalyst, distilling the refluxed mixture and recovering a reaction product containing 1-methyl-1,3-cyclohexadiene.

4 Claims, No Drawings

FLAVOR AND FRAGRANT COMPOSITIONS

This is a division of application Ser. No. 414,394 filed Nov. 9, 1973 now U.S. Pat. No. 3,989,765 which is a division of 125,792 filed Mar. 18, 1971 now abandoned.

The invention relates to flavor and fragrant compositions which are synthetic substitutes for steam-distilled lime oil. These compositions simulate the odor and taste of steam-distilled lime oil.

Creams, lotions, soap, and a variety of household products and similar compositions are generally blended with perfume mixtures containing at least one ingredient selected to impart a pleasing odor. Often, lime oils are selected to impart their characteristic fragrance or flavor. For example, lime odor is desirable in many cosmetic and household compositions, and a lime taste is desired in many soft drinks, candies, foods, ice cream, confectionery, and similar products.

Lime oil is obtained commercially by either the steam distillation of or by the expression (centrifugation) of the macerated sour lime or Mexican lime. Most of the lime oil used commercially is obtained by the distillation method. The essential oil of lime is in the peel of the fruit. Depending upon the condition and the size of the fruit, a barrel of limes, which contains 160 pounds of limes, yields normally about 8 ounces of distilled oil. Diseases, insect pests, and hurricanes grossly affect the supply of lime fruit and, in turn, the production of essential oil of lime. As a result, the lime oil quantity and quality vary each year. The process of production is cumbersome and expensive because it involves growing and harvesting the fruit and delivering it to the point of processing where the fruit is macerated and distilled in unsophisticated equipment.

As a result of the present discovery, the disadvantages of dependence upon natural sources subject to weather conditions and to crop diseases causing limited production are overcome by the present invention of a synthetic substitute for distilled lime oil. It has been discovered that the reaction-product mixture resulting from the acid catalyzed rearrangement of citral has a lime-like fragrance. This fragrance resembles the typical fresh terpenic character of steam-distilled lime oil. The lime "gassy" note of distilled lime oil is provided by a strongly odorous hydrocarbon isolated from the volatile fraction of distilled lime oil and characterized as 1-methyl-1,3-cyclohexadiene. Lime "gassy" note is the odor one gets from smelling the gas, e.g., light, ethereal, fleeting, and with a lime character.

Broadly, the invention relates to a process for making compositions having the flavor and fragrance of steam-distilled natural lime oil which comprises adding an effective amount of the reaction-product mix obtained from the acid-catalyzed rearrangement of citral to a carrier material in which the flavor or fragrance of said lime oil is desired, said carrier being a synthetic substitute for said natural lime oil.

The invention relates, then, to the use of the reaction-product mix resulting from the acid rearrangement of citral as a flavor or fragrant component where a lime topnote is desired. The reaction-product contains a major amount of terpene hydrocarbons and a minor amount of oxygen containing compounds. It may be the sole ingredient of the flavor and/or fragrant component or it may be blended with other aromatic raw materials. Generally the reaction-product mix is present in flavor or fragrant compositions in amounts varying from about 0.5% to 100% by weight of the flavor or fragrant composition. The resulting flavor or fragrant composition may be incorporated in a suitable carrier material, depending upon whether the final product is a cream, lotion, soap, mouthwash, dentrifice, detergent, cleanser, liquid soap for dishes, soft drink or others. Suitable carrier materials are water, alcohol, mineral oil, lanolin, almond oil, sterols, glycerine, sorbitol, propylene glycol, diethyl phthalate, and fluorinated hydrocarbons, such as monochlorodifluoromethane, dichlorotetrafluoroethane, trichloromonofluoromethane. Generally the flavor or fragrant composition, containing reaction-product mix alone or blended with other aromatic materials, is incorporated into suitable carrier material in amounts varying from about 0.5% to about 10% by weight of the total composition containing flavor or fragrant component, carrier and any additives if desired.

The invention also relates to the employment of 1-methyl-1,3-cyclohexadiene, separately from other ingredients in the reaction-product mix, in flavor and fragrant compositions where the lime "gassy" note of steam-distilled lime oil is desired. The cyclohexadiene is generally incorporated in flavor or fragrant compositions in the amount of about 0.5% to 100% by weight of said compositions. The resulting composition is generally incorporated into suitable carrier material, as described above, in an amount of 0.1% to 10% by weight of the total composition of flavor or fragrant component and carrier including any additives, if desired.

It has been found, in accordance with the invention, that the reaction-product mix resulting from the rearrangement of citral is an effective and practical substitute for steam-distilled lime oil wherever the natural product is used or may be used. Its similarity to lime oil makes it useful in providing this citrus effect or "lift" to the perfumes in which it is incorporated. The resulting product mixture may be used in a variety of compositions and in particular perfumes and flavors. Also, in accordance with the invention, the aforesaid 1-methyl-1,3-cyclohexadiene may be blended, without the other terpene hydrocarbon compounds present in the product mix, with other ingredients to form both fragrant and flavor mixtures.

The reaction-product of the present invention may be prepared by distilling an acid mixture of citral and water. Preferably, the acid mixture of citral and water is heated at a temperature of 25° to 100° C for .5 to 5 hours, prior to steam distillation. Most preferably, the acidic citral-water mixture is refluxed for 1 to 3 hours prior to distillation as this process gives a 70% to 75% yield based on the citral component.

The citral used in the reaction may be either natural or synthetic. Natural citral is obtained from the distillation of lemongrass oil which is produced in India and Guatemala. Eucalyptus staigeriana and Litsea cubeba are also natural sources for citral. Synthetic citral may be prepared by the Hoffman-La Roche process disclosed in U.S. Pat. No. 2,795,617. It is not necessary to use pure citral since it would be possible to achieve the same reaction using oils with a significant citral content. The use of oils from lemongrass, Eucalyptus staigeriana or Litsea cubeba as sources of citral would result in a modification of the lime character of the reaction product to the extent of the additional notes from the impurities.

A number of acids are suitable for the acid rearrangement of citral, for example, the mineral acids such as hydrochloric, phosphoric and sulfuric and organic acids such as benzoic, oxalic, tartaric, malic, maionic and citric. The preferred acids are citric and hydrochloric. The pH of the acidic citral-water mixture is generally below pH 5.5, and preferably below pH 3.5.

EXAMPLE 1

A preferred synthetic substitute for distilled lime oil is prepared as follows.

Citral (30.0 grams) is added to 250 milliliters of a citric acid solution (pH 1.75) prepared by dissolving 36.0 grams of citric acid (analyzed anhydrous powder) in distilled water to a 500-milliliter volume. This mixture is refluxed mildly for two hours in a single-neck 500-milliliter flask. After two hours the flask is equipped with a condenser and a lighter-than-water collection trap, and the product is water-distilled. The yield of distilled lime product is 22.0 grams (73%). The remaining nondistillable product is highly resinous and does not possess the lime-like fragrance. The distillable product mix contains about 60% terpene hydrocarbons, about 35% unidentified oxygen-containing compounds, and the remainder additional hydrocarbons. About 5% of the product mix is the terpene hydrocarbon 1-methyl-1,3-cyclohexadiene. Also present are trace amounts of 3-methylene-1-cyclohexene; 1-methyl-1,5-cyclohexadiene; isoprene, n-heptane; isopropyl formate; acetone and isopropanol.

A number of variations to the acid-catalyzed rearrangement process are permissible. Both natural and synthetic citral may be used in the reaction. It is not necessary to use pure citral, but material containing a significant amount of citral is perfectly acceptable. Other acids set out above may be substituted for citric acid. It is to be noted that the acid is acting as a catalyst in the reaction and is not consumed so that it may be recovered at the end of the reaction. The amount of citral may be varied depending upon the amount of synthetic lime-mix product desired. Generally, the weight ratio of citral to acid is from about 1:1 to 20:1. The pH of the reaction may also be varied as previously stated. An adjusted pH between 1.0 – 2.0 is most preferred.

Although the presently preferred method is to reflux for two hours, both time and temperature may be varied by one skilled in the art and the desired product mix will still be obtained. Citral may also be rearranged without refining at all but with vigorous agitation in acidic medium at 25° C for approximately 4 to 6 hours.

One of the important ingredients of the synthetic lime mix is the 1-methyl-1,3-cyclohexadiene. This material provides the characteristic "gassy" note of lime oil. Although it is difficult to obtain the 1-methyl-1,3-cyclohexadiene from the synthetic lime oil mix of this invention, several practical methods of preparation have been reported in the literature; and the method of A. J. Birch reported in the Journal of the Chemical Society of 1947 on page 1642 is a practical method for obtaining this isomer.

The lime synthetic mix of the instant invention can be used very effectively with blends containing any of the following aromatic raw materials: lavender/lavandin, rosemary, cyclamen, aldehyde, geraniol, citronellol, phenyl ethyl alcohol, and coumarin. Also see Examples 2–12 for many other aromatic raw materials. This synthetic mix adds a fresh topnote to colognes and is especially useful in providing life to sweet-heavy perfume blends.

To illustrate the applicability of the synthetic lime mix of this invention, a number of examples of flavor or fragrant compositions or blends containing the steam-distilled lime-oil substitute are set out below. Examples 2–12 show lime flavor or fragrant compositions comprising blends of reaction-product mix or 1-methyl-1,3-cyclohexadiene with other aromatic raw materials.

EXAMPLE 2

A fragrant mixture suitable for incorporation into hand lotions, cream, and dishwashing formulations contains the following ingredients in the parts by weight indicated:

| Ingredient | Percent |
| --- | --- |
| Benzaldehyde | 55.0 |
| *Synthetic lime mix of Example 1 | 10.0 |
| Phenylethyl alcohol | 10.0 |
| Orange oil | 3.0 |
| Lemon oil | 3.0 |
| α- Ionone | 5.0 |
| Citronellol | 4.0 |
| Coumarin | 3.0 |
| Linalool | 2.0 |
| Spike lavender | 1.0 |
| Cinnamic aldehyde | 1.0 |
| Benzyl acetate | 2.0 |
| Geranium bourbon | 1.0 |
| | 100.0 |

*or 1-methyl-1,3-cyclohexadiene

EXAMPLE 3

A fragrant mixture suitable for incorporation into soap, shampoo, and detergent formulations contains the following ingredients in the parts by weight indicated:

| Ingredient | Percent |
| --- | --- |
| *Synthetic lime mix of Example 1 | 10.0 |
| Rosemary Spain | 20.0 |
| Lavender | 15.0 |
| Clove stem | 10.0 |
| Galaxolide (I.F.F. registered) | 4.0 |
| Vetiver Haitian | 3.0 |
| Vertenex (I.F.F. registered) | 3.0 |
| Heliotropine | 3.0 |
| Linalool | 5.0 |
| Benzyl acetate | 6.0 |
| Coumarin | 1.0 |
| Cedarwood Virginia | 10.0 |
| Vertofix (I.F.F. registered) | 5.0 |
| Geranium bourbon | 5.0 |
| | 100.0 |

*or 1-methyl-1,3-cyclohexadiene

EXAMPLE 4

A fragrant mixture suitable for incorporation into cleanser and detergent formulations contains the following ingredients in the parts by weight indicated:

| Ingredient | Percent |
| --- | --- |
| *Synthetic lime mix of Example 1 | 15.0 |
| Tetrahydromuguol (I.F.F. registered) | 15.0 |
| Phenylethyl alcohol | 15.0 |
| Bois de Rose | 10.0 |
| Geranium bourbon | 5.0 |
| Coumarin | 3.0 |
| Terpineol | 3.0 |
| Cinnamic alcohol | 5.0 |
| Amyl cinnamic aldehyde | 5.0 |
| Petitgrain | 2.0 |
| Citral | 2.0 |
| Orange crystals | 2.0 |

-continued

| Ingredient | Percent |
|---|---|
| Citronella Java | 2.0 |
| Musk ketone | 2.0 |
| Lemon oil | 1.0 |
| Geraniol | 5.0 |
| Citronellol | 5.0 |
| Lemon terpenes | 2.0 |
| Cyclamen aldehyde | 1.0 |
| | 100.0 |

*or 1-methyl-1,3-cyclohexadiene

EXAMPLE 5

A perfume blend having a lime fragrance suitable for adding to cologne and shaving-cream formulations contains the following ingredients in the parts by weight indicated:

| Ingredient | Percent |
|---|---|
| Cedarwood Virginia | 13.0 |
| Vertofix (I.F.F. registered) | 10.0 |
| Vertenex (I.F.F. registered) | 5.0 |
| *Synthetic lime mix of Example 1 | 10.0 |
| Bergamot | 20.0 |
| Tonka beam resin | 3.0 |
| Vetiver bourbon | 5.0 |
| Patchouli | 3.0 |
| Clove bud oil | 3.0 |
| Lavender | 8.0 |
| Rosemary | 3.0 |
| Lemon oil | 3.0 |
| Lavandin | 3.0 |
| Sandalwood | 3.0 |
| Galbanum | 1.0 |
| Cedrenyl methyl ether | 3.0 |
| α - Ionone | 2.0 |
| Musk ketone | 1.0 |
| Cinnamon leaf | 0.5 |
| Celery seed oil (1% ethanol solution) | 0.5 |
| | 100.0 |

*or 1-methyl-1,3-cyclohexadiene

As a flavor ingredient, the synthetic lime-oil mix can be used to replace commercial distilled lime oil in dental cream flavors, cola-type flavors, mouthwash flavors, "7-up"-type flavors, "Juicy Fruit" flavors, banana-type flavors, blends with lemon flavors.

EXAMPLE 6

A flavor mix containing the synthetic lime substitute suitable for cola-type flavors contains the following ingredients in the parts by weight indicated:

| Ingredient | Percent |
|---|---|
| *Synthetic lime mix of Example 1 | 9.0 |
| Vanilla extract | 0.6 |
| Solid extract Kola nuts | 2.0 |
| Kola flavor emulsion | 17.4 |
| Caramel | 71.0 |
| | 100.0 |

*or 1-methyl-1,3-cyclohexadiene

EXAMPLE 7

A flavor mix suitable for dental cream or mouthwash formulations contains the following ingredients in the parts by weight indicated:

| Ingredients | Percent |
|---|---|
| *Synthetic lime mix of Example 1 | 2.0 |
| Anethole | 5.0 |
| Carvone | 30.0 |
| Spearmint oil | 23.0 |
| Peppermint oil | 40.0 |

| Ingredients | Percent |
|---|---|
| | 100.0 |

*or 1-metyl-1,3-cyclohexadiene

EXAMPLE 8

Another flavor mix suitable for dental cream or mouthwash formulations contains the following ingredients in the parts by weight indicated:

| Ingredients | Percent |
|---|---|
| *Synthetic lime mix of Example 1 | 10.0 |
| Cinnamic aldehyde | 25.0 |
| Clove bud oil | 15.0 |
| Anethole | 5.0 |
| Carvone | 5.0 |
| Menthol | 20.0 |
| Peppermint oil | 20.0 |
| | 100.0 |

*or 1-methyl-1,3-cyclohexadiene

EXAMPLE 9

A flavor mix suitable for lemon-lime formulations contains the following ingredients in the parts by weight indicated:

| Ingredient | Percent |
|---|---|
| *Synthetic lime mix of Example 1 | 25.0 |
| Lemon oil | 75.0 |
| | 100.0 |

*or 1-methyl-1,3-cyclohexadiene

EXAMPLE 10

A flavor mix which is suitable for banana-type formulations contains the following ingredients in the parts by weight indicated:

| Ingredient | Percent |
|---|---|
| *Synthetic lime mix of Example 1 | 2.0 |
| Amyl acetate | 60.0 |
| Amyl butyrate | 10.0 |
| Hexyl acetate | 10.0 |
| Ethyl butyrate | 5.0 |
| Acetaldehyde | 3.0 |
| Ethyl pelargonate | 3.0 |
| Mimosa (1% ethanol solution) | 2.0 |
| Amyl propionate | 5.0 |
| | 100.0 |

*or 1-methyl-1,3-cyclohexadiene

Examples 11 and 12 illustrate fragrant blends which are generally applicable for adding to a variety of formulations:

| Ingredient | Example 11 Percent | Example 12 Percent |
|---|---|---|
| *Synthetic lime mix of Example 1 | 10.00 | 25.00 |
| D-limonene | 65.00 | 50.00 |
| p-Cymene | 10.00 | 5.00 |
| Bisabolene | 1.00 | 1.00 |
| Fenchol | 0.60 | 1.00 |
| Linalool | 0.50 | 1.00 |
| Terpinen-4-ol | 0.50 | 2.00 |
| α-terpineol | 6.00 | 5.00 |
| Borneol | 0.60 | 0.50 |
| Alcohol C-8 | 0.20 | 0.50 |
| Alcohol C-9 | 0.10 | 0.50 |
| Alcohol C-10 | 0.20 | 0.50 |
| Geraniol | 0.50 | 1.00 |

-continued

| Ingredient | Example 11 Percent | Example 12 Percent |
|---|---|---|
| Citral | 1.00 | 0.50 |
| Aldehyde C-8 | 0.20 | 0.20 |
| Aldehyde C-9 | 0.10 | 0.30 |
| Aldehyde C-10 | 0.10 | 0.20 |
| Citronellal | 0.20 | 0.50 |
| 2-hexenal | 0.05 | 0.10 |
| Methyl heptenone | 0.05 | 0.70 |
| Rose oxide | 0.20 | 0.50 |
| Geranyl acetate | 0.50 | 2.00 |
| Cineole | 1.00 | 0.50 |
| Coumarin | 0.40 | 1.50 |
| Ethyl acetoacetate | 1.00 | — |
|  | 100.00 | 100.00 |

*or 1-methyl-1,3-cyclohexadiene

As previously stated, our synthetic lime mix may be incorporated into a variety of products. The following examples are illustrative:

Example 13
Mouthwash

| Ingredients | Percent by Weight |
|---|---|
| Ethyl alcohol | 10.000 |
| Flavor mixtures of Examples 7 or 8 | 0.200 |
| Cetyl pyridinium chloride | .080 |
| Sorbitol (30% solution) | 10.000 |
| Water | 79.519 |
| Saccharin sodium | .200 |
| Color | .001 |
|  | 100.000 |

Example 14
After Shave Lotion

| Ingredients | Percent by Weight |
|---|---|
| Ethyl alcohol | 50.00 |
| Sorbitol | 2.50 |
| Fragrant mixture of Example 5 or 1-methyl-1,3-cyclohexadiene | .60 |
| Boric acid | 2.00 |
| Water | 44.90 |
|  | 100.00 |

Example 15
Aerosol Shave Cream

| Ingredients of Concentrate | Percent by Weight |
|---|---|
| Glycerin | 10.00 |
| Triethanolamine | 4.00 |
| Stearic acid, triple pressed | 4.50 |
| Stripped coconut fatty acids | 1.50 |
| Fragrant mixture of Example 5 or 1-methyl-1,3-cyclohexadiene | .375 |
| Glyceryl monostearate | 5.00 |
| Water | 14.625 |
|  | 100.000 |
| Above concentrate | 93.000 |
| Dichlorotetrafluoromethane/ dichlorotetrafluoroethane 57/43 | 7.000 |
| Final Aerosol Shave Cream Composition | 100.000 |

It is understood that 1-methyl-1,3-cyclohexadiene may be used in perfume and flavoring blends in the absence of the other products of synthetic lime mix. This ingredient can be employed most effectively in a d-limonene solution such as 95% d-limonene and 5% 1-methyl-1,3-cyclohexadiene. It may also be used as indicated in any of the examples recited above as the sole component of the synthetic lime mix; however, it is not limited to these applications and can be used whenever the characteristic "gassy" note of lime oil is desired.

What is claimed is:

1. A method of making a synthetic lime mix having the fragrance of steam distilled natural lime oil comprising the steps of refluxing a mixture of (A) citral or a citral-containing oil selected from the group consisting of lemongrass oil, Eucalyptus staigeriana and Litsea cubeba and (B) an acid selected from the group consisting of mineral acids and organic carboxylic acids and water for a period of from 1 to 3 hours, said acid being a catalyst and being present in a weight ratio of citral to acid of from about 1:1 to 20:1 which is effective to adjust the pH of said mixture to between 1.0 and 2.0; distilling the refluxed mixture and recovering from the distilled mixture a reaction-product consisting essentially of a major amount of terpene hydrocarbons and minor amounts of oxygen-containing compounds and 1-methyl-1,3-cyclohexadiene.

2. A method according to claim 1 wherein said acid is citric acid.

3. A method as defined in claim 1 wherein said mineral acid is selected from the group consisting of hydrochloric acid, phosphoric acid and sulfuric acid and said organic carboxylic acid is selected from the group consisting of benzoic acid, oxalic acid, tartaric acid, malic acid, malonic acid and citric acid.

4. A method according to claim 3 wherein said acid is citric acid or hydrochloric acid.

* * * * *